United States Patent [19]
Myers

[11] Patent Number: 5,798,078
[45] Date of Patent: Aug. 25, 1998

[54] SULFONATED POLYMERS AND METHOD OF SULFONATING POLYMERS

[75] Inventor: David L. Myers, Cumming, Ga.

[73] Assignee: Kimberly-Clark Worldwide, Inc., Neenah, Wis.

[21] Appl. No.: 679,607

[22] Filed: Jul. 11, 1996

[51] Int. Cl.$^6$ .............. B29C 71/04; C08F 8/36; D06B 19/00; D06M 10/06
[52] U.S. Cl. .......... 264/446; 264/83; 8/115.53; 8/115.54; 204/157.64; 204/157.78; 522/127; 522/129; 562/121
[58] Field of Search .............. 264/83, 446; 204/157.64, 204/157.78; 562/121; 522/127, 129; 8/115.51, 115.52, 115.53, 115.54

[56] References Cited

U.S. PATENT DOCUMENTS

| | | | |
|---|---|---|---|
| 3,260,741 | 7/1966 | Mackinnon et al. | 562/121 |
| 3,325,387 | 6/1967 | Black | 204/157.64 |
| 3,338,992 | 8/1967 | Kinney | 264/24 |
| 3,341,394 | 9/1967 | Kinney | 161/72 |
| 3,372,188 | 3/1968 | Alston et al. | 562/121 |
| 3,464,952 | 9/1969 | Larsen . | |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,909,009 | 9/1975 | Cvetko et al. | 275/37 |
| 4,307,143 | 12/1981 | Meitner | 252/91 |
| 4,340,563 | 7/1982 | Appel et al. | 264/518 |
| 4,663,220 | 5/1987 | Wisneski et al. | 428/22 |
| 4,666,452 | 5/1987 | Nohr et al. | 8/115.52 |

FOREIGN PATENT DOCUMENTS

| | | |
|---|---|---|
| 0 207 204 | 1/1987 | European Pat. Off. . |
| 0 340 617 | 11/1989 | European Pat. Off. . |
| 952 111 | 3/1964 | United Kingdom . |
| 1 414 671 | 11/1975 | United Kingdom . |

OTHER PUBLICATIONS

Derwent Abstract for JP 720077827 dated Aug. 3, 1972.

Derwent Abstract for JP 1266224 dated Oct. 24, 1989.

"Getting An Insight Into The Liquid-Phase Sulfonation Of 1-Alkenes: Primary and Secondary Products", Communications presentadas a las Jornadas del Comite Espanal de la Detergencia. vol. 16, 1985, pp. 247-261.

(List continued on next page.)

Primary Examiner—David A. Simmons
Assistant Examiner—Kenneth M. Jones

[57] ABSTRACT

Methods of sulfonating a polymer are provided. One method of sulfonating a polymer includes exposing sulfur dioxide and oxygen to free radical producing energy and contacting the polymer with the product of preceding step. Desirably, the steps of exposing sulfur dioxide and oxygen to free radical producing energy and contacting the polymer with this product are performed in a reduced pressure environment. Another method of sulfonating a polymer includes contacting the polymer with sulfur dioxide and oxygen and exposing the contacted polymer to free radical producing energy. The polymer may be contacted with a mixture of sulfur dioxide and oxygen or the polymer may be separately contacted with sulfur dioxide and oxygen. When the polymer is separately contacted with sulfur dioxide and oxygen, the polymer may first be contacted with sulfur dioxide and then contacted with oxygen. The source of the free radical producing energy may be ultra-violet light, electron beam, noble gas radio frequency (rf) plasma, corona discharge, or gamma radiation.

9 Claims, 1 Drawing Sheet

OTHER PUBLICATIONS

"Formation and Reaction of Polyenesulfonic Acid. I. Reaction of Polyethylene Films with $SO_3$", Journal of Polymer Science: Part A: Polymer Chemistry, vol. 26, 1988, pp. 167–176.

"Sulfonation of Polyethylene Membranes", Journal of Applied Polymer Science, Fol. 42, 1991, pp. 1285–1287.

"Formation and Reaction of Polyenesulfonic Acid. II. Photoreaction of Polyenesulfonic Acids", Journal of Polymer Science: Part A: polymer Chemistry, vol. 26, 1988, pp. 177–185.

"Formation and Reaction of Polyenesulfonic Acid. III. Preparation and Photoreaction of 1,3,5-Hexatriene-1,6-disulfonic Acid", Journal of Polymer Science: Part A: Polymer Chemistry, vol. 26, 1988, pp. 187–194.

"Improving Adhesion To Polymers By Gas Phase Sulfonation", Advanced Composites Conference And Exposition, ASM/ESD, 1993, pp. 241–249.

"Sulfonation And Sulfation", Encyclopedia of Chemical Technology, 3rd Edition, vol. 22, pp. 1–45 (1983).

"Sulfonation of low-density polyethylene films. Infrared absorption coefficients for the sulfonic group", Makromol. Chem. 192, 1991, pp. 491–497.

Kirk–Othmer Encyclopedia of Chemical Technology vol. 22, pp. 18–19.

SULFONATED POLYMERS AND METHOD OF SULFONATING POLYMERS

FIELD OF THE INVENTION

The present invention is directed to surface modified polymers. More particularly, the present invention is directed to sulfonated polymers. Still more particularly, the present invention is directed to gas phase sulfonation of polymers.

BACKGROUND OF THE INVENTION

As is generally known, the surfaces of certain polymers, for example thermoplastic polymers, are inherently non-wettable or hydrophobic. It is also generally known that thermoplastic polymers, for example polyolefin polymers, may be formed into fibers. Such polyolefin fibers may be employed in a variety of commercial applications. For some commercial applications, for example absorbent products, disposable absorbent products and disposable nonwoven absorbent products, the inherent hydrophobic nature of such polymers is a disadvantage. As such, before these inherently hydrophobic polymers may be employed in such absorbent products, the hydrophobic nature of these polymers requires alteration.

One method of altering the hydrophobic nature of such polymers, for example shaped polymers, is sulfonation. As used herein, the term "shaped polymer" or "shaped polymers" means any solid form of a polymer, in contrast to a polymer in gaseous or liquid phase, or in solution. Thus, shaped polymers can be in particulate form, such as powder or granules or chips, a molded article, an extruded shape, fibers, woven or nonwoven fabrics, films, foams or the like. As used herein, the term "sulfonation" means methods of forming a compound containing sulfonic acid, the —$SO_2O$ group. Such methods include, for example, converting organic compounds to sulfonic acids or sulfonates containing the structural group C—$SO_2$—O or in some cases, N—$SO_2$—O.

However, in many instances, conventional sulfonation methods require the use and/or storage of materials which pose both health and safety concerns. Examples of such materials include, for example, sulfur trioxide, concentrated sulfuric acid, oleum, and chlorosulfuric acid. Additionally, in many instances, when polymers, such as, for example the surfaces of polyolefin nonwoven webs, are subjected to conventional sulfonation methods, undesirable surface discoloration may occur. For instance, fibers formed from un-dyed polymers, such as polyolefin fibers and desirably, polypropylene fibers, are generally translucent. After being subjected to conventional sulfonation methods, the surface color of such fibers changes such that the fibers appear generally yellow, brown or black in color. As previously mentioned, such polymers may have applications as absorbent articles. As such, in some instances, the discoloring of polymer fibers is generally not desirable, particularly when such polymer fibers are incorporated into personal absorbent articles, such as diapers, feminine pads, or adult incontinence articles.

Therefore, there is a need for improved methods of sulfonation which avoid the disadvantages of conventional sulfonation processes. Such an improved sulfonation method and the products thereof are provided by the present invention and will become more apparent upon further review of this specification.

SUMMARY OF THE INVENTION

In response to the above problems encountered by those of skill in the art, the present invention provides methods of sulfonating a polymer which avoid storing large quantities of sulfur trioxide, concentrated sulfuric acid, oleum, or chlorosulfuric acid. The methods of the present invention also avoid the undesirable discoloring and, particularly, the undesirable brown coloring, inherent in many conventional sulfonating processes.

In one embodiment of the present invention, the method of sulfonating a polymer includes exposing sulfur dioxide and a source of oxygen to free radical producing energy to produce a product and contacting the polymer with the product of preceding step. Desirably, the steps of exposing sulfur dioxide and the source of oxygen to free radical producing energy and contacting the polymer with this product are performed in a reduced pressure environment. The source of the free radical producing energy may be ultra-violet light, gamma radiation, electron beam, noble gas radio frequency (rf) plasma or corona discharge. The source of oxygen may include oxygen, an oxygen donating gas or a combination thereof.

In another embodiment, the method of sulfonating a polymer includes contacting the polymer with sulfur dioxide and a source of oxygen and exposing the contacted polymer to free radical producing energy. In this embodiment, the polymer may be contacted with a mixture of sulfur dioxide and the source of oxygen or the polymer may be separately contacted with sulfur dioxide and the source of oxygen. When the polymer is separately contacted with sulfur dioxide and the source of oxygen, the polymer may first be contacted with sulfur dioxide and then contacted with the source of oxygen. Desirably, the contacting and exposing steps occur in a reduced pressure, i.e., generally, less than 1 atmosphere, environment. In this embodiment, the source of the free radical producing energy may also be ultra-violet light, gamma radiation, electron beam, noble gas rf plasma or corona discharge. The source of oxygen may include oxygen, an oxygen donating gas or a combination thereof.

Another embodiment of the present invention provides a method of imparting hydrophilic character to a shaped polymer. This method includes exposing sulfur dioxide and a source of oxygen to free radical producing energy and contacting the polymer with the product of the preceding step. Desirably, the contacting and exposing steps occur in a reduced pressure environment. In this embodiment, the source of the free radical producing energy may be ultra-violet light, gamma radiation, electron beam, noble gas rf plasma or corona discharge. The source of oxygen may include oxygen, an oxygen donating gas or a combination thereof.

Another method of imparting hydrophilic character to a shaped polymer includes contacting the polymer with sulfur dioxide and a source of oxygen and exposing the contacted polymer to radical producing energy. Desirably, the contacting and exposing steps occur in a reduced pressure environment. The source of the free radical producing energy may also be ultra-violet light, gamma radiation, electron beam, noble gas rf plasma or corona discharge. The source of oxygen may include oxygen, an oxygen donating gas or a combination thereof.

DETAILED DESCRIPTION OF THE INVENTION

Figure 1:
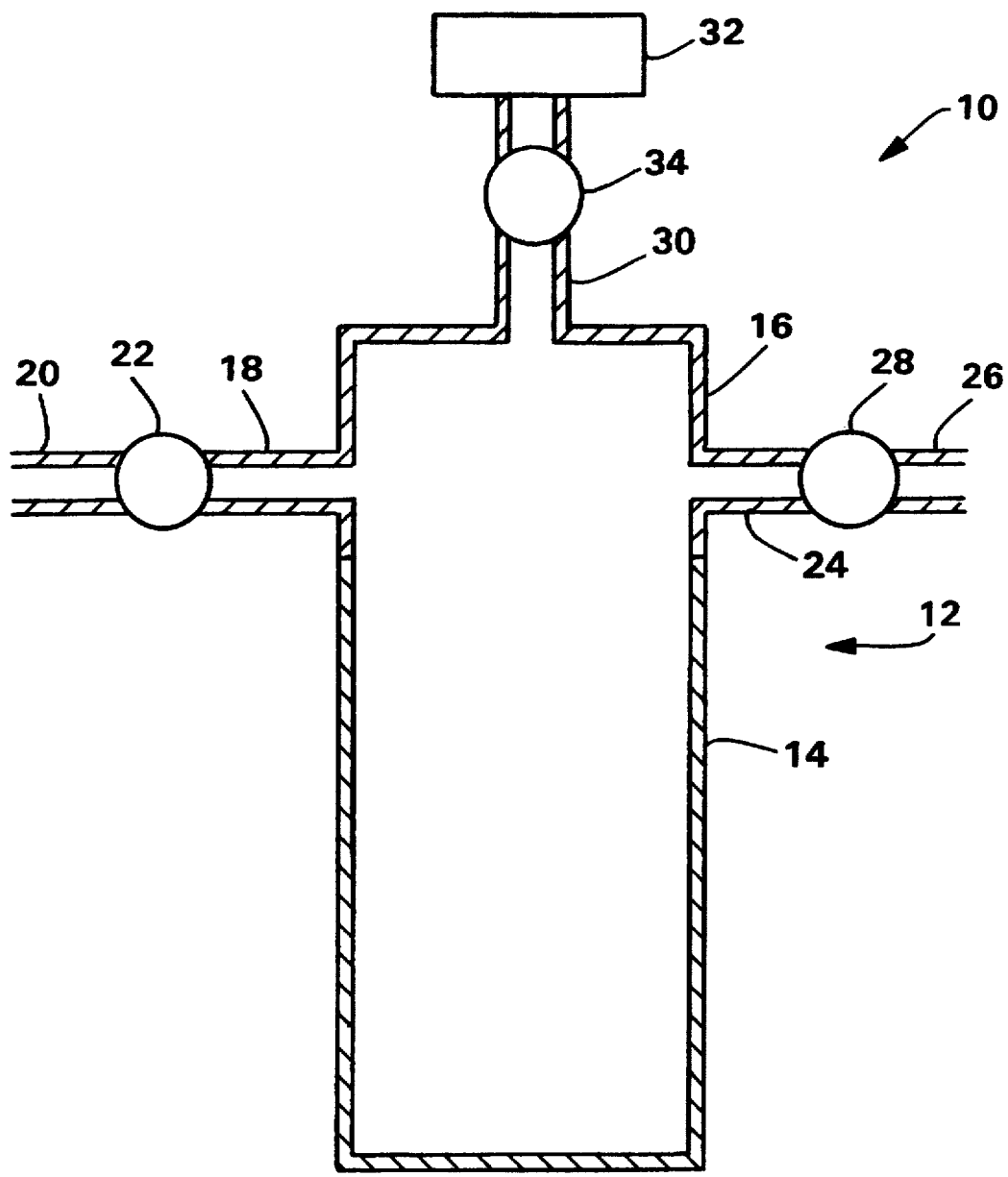
FIG. 1 is a schematic illustration of a reaction chamber.

As used herein, the term "oxygen donating gas" or "source of oxygen" means di-oxygen or a gas which is capable of contributing an oxygen atom or an oxygen radical.

As used herein, the term "free radical producing energy" means any energy which results in homolytic or heterolytic cleavage of at least two covalently bonded atoms.

As used herein, the term "hydrophilic" or "hydrophilic character" when associated with a material, such as, for example, a polymer or shaped polymer, means that the water (deionized, distilled water) contact angle of a droplet of water positioned on the surface of such material is less than 90°.

As used herein, the term "hydrophobic" when associated with a material, such as, for example, a polymer, means that the water (deionized, distilled water) contact angle of a droplet of water positioned on the surface of such material is greater than 90°.

As used herein, the term "polymer" may mean both synthetic or natural polymers. Examples of natural polymeric materials include, cotton, silk, wool, and cellulose, by way of illustration only.

Synthetic polymers, in turn, can be either thermosetting or thermoplastic materials, with thermoplastic materials being more common. Examples of thermosetting polymers include, by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

Examples of thermoplastic polymers include, by way of illustration only, end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly (chlorotrifluoroethylene), ethylene-chlorotrifluoroethylene copolymers, poly(vinylidene fluoride), poly(vinyl fluoride), and the like; polyamides, such as poly(6-aminocaproic acid) or poly(ε-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly (sulfonyl-1,4-phenyleneoxy-1,4-phenylenesulfonyl-4,4'-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly (thio-1,4-phenylene), and the like; polyimides, such as poly (pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; copolymers of the foregoing, such as acrylonitrile-butadiene-styrene (ABS) copolymers, and the like.

As used herein, the term "shaped polymer" or "shaped polymers" means any solid form of a polymer, in contrast to a polymer in gaseous or liquid phase, or in solution. Thus, shaped polymers can be in particulate form, such as powder or granules or chips, a molded article, an extruded shape, fibers, woven or nonwoven fabrics, films, foams or the like.

As used herein, the term "sulfonation" means methods of converting organic compounds to sulfonic acids or sulfonates containing the structural group C—SO$_2$—O or in some cases, N—SO$_2$—O. Sulfonation of a shaped polymer is useful, for example, in altering the surface properties of such shaped polymer. The properties of such surface may be altered, for example, such that the altered surface becomes hydrophilic, is more receptive to the placement of an adhesive thereon, and/or becomes printable.

As used herein, the term "nonwoven fabric" refers to a fabric that has a structure of individual fibers or filaments which are interlaid, but not in an identifiable repeating manner.

As used herein the term "spunbond fibers" refers to fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et. al., and U.S. Pat. No. 3,692,618 to Dorschner et. al., U.S. Pat. No. 3,802,817 to Matsuki et. al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et. al. which are all herein incorporated by reference.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a fabric of randomly disbursed meltblown fibers. Meltblowing is described, for example, in U.S. Pat. No. 3,849,241 to Buntin, U.S. Pat. No. 4,307,143 to Meitner et. al., and U.S. Pat. No. 4,663,220 to Wisneski et. al. which are all herein incorporated by reference.

The sulfonating methods of the present invention avoid the requirement of having or storing quantities of materials, such as, for example, sulfur trioxide, concentrated sulfuric acid, oleum and chlorosulfuric acid, which are traditionally required to initiate conventional sulfonation processes. The methods of the present invention also avoid the inherent brown coloring produced by many conventional sulfonation processes.

In one embodiment of the present invention, the method of sulfonating a polymer includes exposing sulfur dioxide and a source of oxygen to free radical producing energy and contacting the polymer with the product of preceding step.

Desirably, the steps of exposing sulfur dioxide and the source of oxygen to free radical producing energy and contacting the polymer with this product are performed in a reduced pressure environment. The source of the free radical producing energy may be ultra-violet light, gamma radiation, electron beam, noble gas radio frequency (rf) plasma or corona discharge. The source of oxygen may include oxygen, an oxygen donating gas, described in greater detail below, or a combination thereof.

In another embodiment, the method of sulfonating a polymer includes contacting the polymer with sulfur dioxide and a source of oxygen and exposing the contacted polymer to free radical producing energy. In this embodiment, the polymer may be contacted with a mixture of sulfur dioxide and the source of oxygen or the polymer may be separately contacted with sulfur dioxide and the source of oxygen. When the polymer is separately contacted with sulfur dioxide and the source of oxygen, the polymer may first be contacted with sulfur dioxide and then contacted with the source of oxygen. Desirably, the contacting and exposing steps occur in a reduced pressure environment. The source of the free radical producing energy may also be ultra-violet light, gamma radiation, electron beam, noble gas rf plasma or corona discharge. The source of oxygen may include oxygen, an oxygen donating gas, or a combination thereof.

Another embodiment of the present invention provides a method of imparting hydrophilic character to a shaped polymer. This method includes exposing sulfur dioxide and a source of oxygen to free radical producing energy and contacting the polymer with the product of preceding step. Desirably, the contacting and exposing steps occur in a reduced pressure environment. The source of the free radical producing energy may be ultra-violet light, gamma radiation, electron beam, noble gas rf plasma or corona discharge. The source of oxygen may include oxygen, an oxygen donating gas, or a combination thereof.

Another method of imparting hydrophilic character to a shaped polymer includes contacting the polymer with sulfur dioxide and a source of oxygen and exposing the contacted polymer to radical producing energy. Desirably, the contacting and exposing steps occur in a reduced pressure environment. The source of the free radical producing energy may also be ultra-violet light, gamma radiation, electron beam, noble gas rf plasma or corona discharge. The source of oxygen may include oxygen, an oxygen donating gas, or a combination thereof.

In the above embodiments, the concentrations of sulfur dioxide and oxygen are not critical, provided that such concentrations are sufficient to impart the desired degree of sulfonation and/or hydrophilic character to the polymer. Generally, the concentration of sulfur dioxide and oxygen are sufficient when either the amount of $SO_2$ present exceeds the amount of oxygen ($O_2$), or when the concentrations of $SO_2$ and $O_2$ are stoichiometric. In either case, it is desirable to avoid the presence of excess quantities of oxygen, i.e., quantities of oxygen greater than stoichiometric quantities, in the reaction atmosphere during the sulfonation reaction.

In addition, the reaction atmosphere may be anhydrous or the reaction atmosphere may be substantially or relatively water-free. In the later instance, small amounts of residual water may be removed by the formation of $SO_3$ during the reaction. The $SO_3$ reacts with the water to produce sulfuric acid. With a sufficient quantity of $SO_2$ and $O_2$ present in the reaction atmosphere to both dehydrate the reaction atmosphere and sulfonate the polymer substrate, the presence of residual water may not effect the outcome of the sulfonation reaction.

The relative ratios of $SO_2$ to $O_2$ for carrying out the methods of the present invention may be expressed as mole ratios. The minimal mole ratio of $SO_2$ to $O_2$ for the sulfonation methods of the present invention is 2:1 (i.e. exactly stoichiometric). Desirably, the mole ratios may be expressed in whole numbers. Furthermore, at the mole ratio of 2:1 of $SO_2$ to $O_2$, the sulfonation reaction will succeed in producing a sulfonated polymer generally free of yellowing or discoloration. Desirably, the range of mole ratios of $SO_2$ to $O_2$ may range from 2:1 to 5:1.

In addition, an oxygen donating gas may be used in place of all or part of the $O_2$ requirement in the $SO_2$ and $O_2$ blend. For example, nitrous oxide, an example of an oxygen donating gas, could be substituted for all or part of the $O_2$ requirement in the sulfonating process. Other oxygen donating gases may include, for example, nitrogen dioxide and the halogen dioxides like chlorine dioxide. It will be further understood that one or more oxygen donating gases with or without $O_2$ may be employed provided, the overall stoichiometries of $SO_2$ to the other oxygen and/or oxygen donating gases conform to the $SO_2$ to $O_2$ mole ratios expressed above.

Inert gases may also be employed in the sulfonation methods of the present invention. In one embodiment of a low pressure gas phase sulfonation process, an inert gas may be blended with $SO_2$ and $O_2$ and/or oxygen donating gas(es). Alternatively, an inert gas may be used to flush less desirable gases, such as air, from the reaction atmosphere and/or article, such as a porous or fibrous web, prior to initiating the sulfonation reaction. In those instances when the inert gas is used to flush the reaction atmosphere and/or article, the pressure of the reaction atmosphere may either be below one atmosphere (reduced pressure), or at or above one atmosphere. Examples of inert gases include nitrogen, argon, helium, and krypton. Of these inert gases, argon is capable of excluding oxygen due to its atomic weight and density.

In another embodiment, the use of argon gas may provide a continuous sulfonation process. In this instance, the article, such as a fibrous web, is purged with an argon gas stream to remove the air entrained therein. The essentially air-free web may then pass into a UV chamber having a blend of $SO_2$, $O_2$ (or other source of oxygen), and Ar for irradiation, and sulfonation.

The quantities of $SO_2$ and $O_2$ are best expressed as mole fractions. This provides flexibility by not limiting the size of the reaction atmosphere. Thus, in the event the polymer is separately contacted with $SO_2$ and $O_2$, the mole fraction range of total gas present as sulfur dioxide is from about 0.83 to about 0.2. Particularly, in the event the polymer is separately contacted with $SO_2$ and $O_2$, the mole fraction of total gas present as sulfur dioxide may be about 0.83 and desirably about 0.8, and more desirably about 0.75, and most desirably 0.67. The corresponding mole fraction range of oxygen is about 0.17 to about 0.33. Particularly, the mole fraction of oxygen may be about 0.17, and desirably 0.2, and more desirably 0.25, and most desirably 0.33. In the event a different oxidizing gas is substituted for oxygen, the mole fraction of that gas would be determined by the stoichiometry of the reaction leading to the formation of the $SO_3$.

Polymers and desirably, shaped polymers, and more desirably, fabrics formed from polymer fibers are useful in the practice of the present invention. Such polymer fabrics may be either woven or nonwoven. Nonwoven fabrics can be made from a variety of processes including, but not limited to, air laying processes, wet laid processes, hydroentangling processes, spunbonding, meltblowing, staple fiber carding and bonding, and solution spinning. The fibers themselves can be made from a variety of polymer materials, including, but not limited to, polyesters, polyolefins, nylons and copolymers of these materials. The fibers may be relatively short, staple length fibers, typically less than 3 inches, or longer more continuous fibers such as are typically produced by a spunbonding process. It should be noted, however, that shaped polymers other than wovens or nonwovens may be used. Examples of such other shaped polymers include, films, foam/film laminates and combinations hereof, with and without woven or nonwovens.

Furthermore these fabrics may be formed from a single layer or multiple layers. In the case of multiple layers, the layers are generally positioned in a juxtaposed or surface-to-surface relationship and all or a portion of the layers may be bound to adjacent layers. Examples of such nonwoven fabrics formed from such fibers are the polypropylene nonwoven fabrics produced by the Assignee of record, Kimberly-Clark Corporation To demonstrate the attributes of the present invention, the following Examples are provided.

BACKGROUND

The quartz reactor 10 shown in FIG. 1 was used for the sulfonation of the samples described in Examples 1–5. The quartz reactor 10 is formed from optical grade fused quartz a product of Technical Glass Products, Inc., Ohio. The quartz reactor 10 includes a reactor housing 12 having separable top and bottom portions, 14 and 16 respectively, for selectively placing and removing samples into the interior of the reaction housing 12. The top portion 14 further includes a vacuum port 18 connected to a vacuum source 20 by valve 22, a gas port 24 connected to a gas source 26 by valve 28, and a port 30 connected a pressure sensor 32, such as a capacitance manometer model no. CM100, manufactured by Leybold Inficon, Inc., N.Y., by valve 34.

Surface Analysis

All ESCA (Electron Spectroscopy for Chemical Analysis) data were collected with a Surface Science Instruments M-Probe ESCA Spectrometer. Spectral collections were performed with monochromatic aluminum x-ray excitation of an 800 micron area of each sample. Differential charging of samples was compensated using a low energy (1 eV) flux of electrons from an electron flood gun.

Surface Tensions for Wetting

The surface tensions for wetting were evaluated using a Wetting Tension Test Kit, Model STT 11-1 from Pillar Technologies, Inc., Hartland, Wis. The surface tension for wetting was taken as the surface tension of the fluid which spontaneously absorbed into the fibrous nonwoven substrates. The Wetting Tension Kit conforms to ASTM Standard D2578-67.

Contact Angle

Contact angle measurements were made using a Rame-Hart Model 100-06 NRL Contact Angle Goniometer. The contact angle is taken as the line tangent to the edge of a fluid droplet in contact with the substrate surface. The contact angle values were derived by averaging the observations taken from a minimum of three droplets. Each droplet produced a pair of observations.

EXAMPLE 1

Sulfonation of Polypropylene Meltblown

A sample of 0.5 ounces per square yard (osy) polypropylene meltblown (PP MB) material was placed in the quartz reactor 10 shown in FIG. 1. With the sample positioned in the bottom portion 16, the reactor housing 12 was evacuated via the vacuum port 18 to less than $1 \times 10^{-3}$ Torr total pressure. After 5 min the reactor housing 12 was back-filled via gas port 24 with an inert gas ($N_2$ or Ar) to a pressure of 760 Torr. The reactor housing 12 was then re-evacuated. The cycles of back filling and evacuating were repeated three times and concluded with a final evacuation of the reactor housing 12 to a pressure of less than $1 \times 10^{-3}$ Torr total pressure. The final evacuation was followed by introduction into the reactor housing 12 via gas port 24 of a sulfur dioxide ($SO_2$) and oxygen ($O_2$) gas mixture to a total pressure of 200 Torr. The ratio of $SO_2$ to $O_2$ partial pressures in the gas mixture was 2:1. The reactor was then placed in an annular ultraviolet light reactor (Rayonet Photochemical Reactor, The Southern New England Ultraviolet Company) equipped with 16 low pressure mercury lamps. Each lamp had a principle emission wavelength of 254 nm. The combined output of all 16 lamps, measured at the center of the reactor chamber, was 6 milliwatts per centimeter squared (mW/cm$^2$).

The UV irradiation time (Reaction Time) for individual PP MB samples was varied from 5 min to 15 min. Following UV irradiation the reactor was purged with inert gas ($N_2$ or Ar), via gas port 24, to remove residual $SO_2$ or $SO_3$.

5 Minute Reaction Time. The PP MB material was white in color and was wettable to an aqueous test solution with a surface tension of 56 dyne/cm. A PP MB control was wettable to a test solution with a surface tension of 35 dyne/cm. Surface analysis of the sulfonated meltblown PP using ESCA revealed the following surface atomic composition: 88.3 atom % carbon, 9.2 atom % oxygen, and 2.5 atom % sulfur.

10 Minute Reaction Time. The PP MB material was white in color and was wettable to an aqueous test solution with a surface tension of 72 dyne/cm (i.e. equivalent to water). Surface analysis of this sulfonated meltblown using ESCA revealed the following surface atomic composition: 88.5 atom % carbon, 9.2 atom % oxygen, and 2.3 atom % sulfur.

15 Minute Reaction Time. The PP MB material was very faint brown in color and was wettable to an aqueous test solution with a surface tension of 72 dyne/cm (i.e. equivalent to water). Surface analysis of this sulfonated meltblown using ESCA revealed the following surface atomic composition: 84.9 atom % carbon, 12.1 atom % oxygen, and 3.0 atom % sulfur.

Each of the reaction times yielded materials with significantly altered surface properties in comparison with the control meltblown polypropylene. The ESCA data acquired from each sample provides evidence for the incorporation of sulfur on the surface of each material. The sulfur is present as sulfonic acid. This indicates that a carbon to sulfur bond formed in the sulfonation process leading the formation of R—$SO_3H$ groups.

EXAMPLE 2

Sulfonation of Polyethylene Meltblown

The experimental procedure used to sulfonate polyethylene meltblown (PE MB) was the same as outlined in Example 1. In this example a sample of 6 osy PE MB was irradiated in the $SO_2O_2$ atmosphere for 5 min.

The PE MB material was white in appearance after sulfonation. The material was wettable to an aqueous test solution with a surface tension of 72 dyne/cm (i.e. equivalent to water). For comparison, a control non-sulfonated PE MB was wettable to only a 36 dyne/cm test solution. Surface analysis of the PE MB using ESCA indicated the following surface composition: 95.4 atom % carbon, 3.5 atom % oxygen, and 1.1 atom % sulfur. The appearance of sulfur on the surface indicates its incorporation into the surface of the material. The sulfur is present as sulfonic acid.

EXAMPLE 3

Sulfonation of Cellulose

The experimental procedure used to sulfonate cellulose was the same as outlined in Example 1. The cellulose substrate was a Whatman Type 1 Filter Paper. In this example a sample of the cellulose was irradiated in the $SO_2/O_2$ atmosphere for 10 min.

The cellulose substrate was white following sulfonation. A comparison of surface tension for wetting failed to reveal any difference in the cellulose substrate before and after sulfonation. The sulfonated cellulose had a slight sulfur-like odor. This odor was effectively removed by washing in deionized water and drying at 80° C.

Surface compositions (ESCA) of a non-sulfonated cellulose control, the sulfonated cellulose, and the water washed sulfonated cellulose are summarized in Table 1.

TABLE 1

Surface Atomic Composition of Cellulose

| Sample | Percent Atomic Composition (atom %) | | | |
|---|---|---|---|---|
| | Carbon | Oxygen | Sulfur | Fluorine |
| Non-Sulfonated Cellulose Control | 59.0 | 40.2 | 0.0 | 0.8 |
| Sulfonated | 59.2 | 38.2 | 0.9 | 1.8 |
| Sulfonated Water Washed | 57.2 | 39.4 | 1.2 | 2.2 |

The ESCA analysis of the cellulose samples clearly shows the incorporation of sulfur in the cellulose surface. The sulfur appears to be present as sulfonic acids. The presence of fluorine may be attributed to either a fluorochemical additive in the Whatman Filter paper, or to fluorochemicals present in the high vacuum grease used to seal the quartz reactor tube (see FIG. 1).

EXAMPLE 4

Sulfonation of Polyethylene Terephthalate Fibers

The experimental procedure used to sulfonate polyethylene terephthalate (PET) fibers was the same as outlined in Example 1. The PET fibers were irradiated for 10 min in the $SO_2/O_2$ atmosphere described in Example 1.

The sulfonated PET fibers were white in color. The sulfonated PET fibers were wettable to an aqueous solution with a surface tension of 72 dyne/cm (i.e. equivalent to water). For comparative purposes, non-sulfonated control PET fibers were wettable to an aqueous solution with surface tension of 56 dyne/cm and the contact angle of water was observed to be greater than 90°. A contact angle for water on the sulfonated fibers could not be measured due to spontaneous absorption of the water droplet. Water washing of the sulfonated PET fibers and drying at 80° C. did not alter their wettability.

The surface composition (ESCA) of the PET fibers is summarized in Table 2.

TABLE 2

Surface Atomic Composition of PET

| Sample | Percent Atomic Composition (atom %) | | | |
|---|---|---|---|---|
| | Carbon | Oxygen | Sulfur | Fluorine |
| Control PET Fibers | 75.2 | 24.8 | 0.0 | 0.0 |
| Sulfonated PET Fibers | 66.0 | 28.2 | 2.5 | 3.3 |
| Water Washed Sulfonated PET Fibers | 70.2 | 26.8 | 1.5 | 1.6 |

The ESCA analysis clearly shows the incorporation of sulfur into the PET fiber surfaces. The sulfur is present as sulfonic acids. The fluorine present on the sulfonated and water washed sulfonated fibers is due to the high vacuum grease used in sealing the quartz tube reactor.

EXAMPLE 5

Sulfonation of Polystyrene

The experimental procedure used to sulfonate polystyrene (PS) film was the same as outlined in Example 1. The PS film was irradiated for 10 min in the $SO_2/O_2$ atmosphere.

The sulfonated polystyrene film was noticeably yellowed compared to the non-sulfonated control. The water contact angle on the sulfonated PS film was effectively 0°, and the water droplet spread spontaneously to a film. The water contact angle on the non-sulfonated PS film was 92°. A water wash of the sulfonated PS film did not alter its water wettability.

The surface composition (ESCA) of the sulfonated PS film is summarized in Table 3.

TABLE 3

Surface Atomic Composition of PS

| Sample | Percent Atomic Composition (atom %) | | | |
|---|---|---|---|---|
| | Carbon | Oxygen | Sulfur | Fluorine |
| Control PS Film | 95.7 | 2.6* | 0.0 | 0.0 |
| Sulfonated PS Film | 66.5 | 22.2 | 7.6 | 3.7 |
| Water Washed Sulfonated PS Film | 69.0 | 20.6 | 7.8 | 2.6 |

*-Also detected 1.12 atom % silicon and 0.6 atom % chlorine.

Ideally, the control PS film should have a surface composition of around 100 atom % carbon. The silicon, chlorine, and oxygen observed on the control are present due to handling of the film sample. The large increase in atomic percent composition of oxygen and sulfur in the sulfonated PS film is a clear evidence that sulfonation has drastically altered the PS surface. The sulfur is present as sulfonic acid groups. Again, the fluorine is due to surface contamination by the high vacuum grease used in the quartz tube reactor.

While the invention has been described in detail with respect to specific embodiments thereof, it will be appreciated that those skilled in the art, upon attaining an understanding of the foregoing, may readily conceive of alterations to, variations of and equivalents to these embodiments.

What is claimed is:

1. A method of sulfonating a polymer, the method comprising:

contacting the polymer with a gaseous mixture consisting essentially of sulfur dioxide and an oxygen donating gas, in which the mixture has a mole ratio of sulfur dioxide to the oxygen donating gas which is equal to or greater than a stoichiometric ratio; and continuously exposing the polymer and gaseous mixture to ultraviolet light while the polymer is in contact with the gaseous mixture; wherein contacting and exposing are carried out at a pressure of less than 1 atmosphere and the oxygen donating gas is nitrous oxide, nitrogen dioxide, or a halogen dioxide.

2. The method of claim 1 wherein the gaseous mixture is anhydrous.

3. The method of claim 1, wherein the ultraviolet light has a principle wavelength of 254 nm.

4. A method of imparting hydrophilic character to a shaped polymer, the method comprising:

contacting the shaped polymer with a gaseous mixture consisting essentially of sulfur dioxide and an oxygen donating gas, in which the mixture has a mole ratio of sulfur dioxide to the oxygen donating gas which is equal to or greater than a stoichiometric ratio; and continuously exposing the shaped polymer and gaseous mixture to ultraviolet light while the shaped article is in contact with the gaseous mixture; wherein contacting and exposing are carried out at a pressure of less than 1 atmosphere and the oxygen donating gas is nitrous oxide, nitrogen dioxide, or a halogen dioxide.

5. The method of claim 4, wherein the gaseous mixture is anhydrous.

6. The method of claim 4, wherein the ultraviolet light has a principle wavelength of 254 nm.

7. A method of sulfonating a polymer, the method comprising:

continuously exposing a gaseous mixture consisting essentially of sulfur dioxide and an oxygen donating gas to ultraviolet light, in which the mixture has a mole ratio of sulfur dioxide to the oxygen donating gas which is equal to or greater than a stoichiometric ratio; and contacting the polymer with the exposed gaseous mixture; wherein exposing and contacting are carried out at a pressure of less than 1 atmosphere, continuous exposure is carried out for as long as the exposed gaseous mixture is in contact with the polymer, and the oxygen donating gas is nitrous oxide nitrogen dioxide, or a halogen dioxide.

8. The method of claim 7, wherein the gaseous mixture is anhydrous.

9. The method of claim 7, wherein the ultraviolet light has a principle wavelength of 254 nm.

* * * * *